United States Patent [19]
Herrmann et al.

[11] Patent Number: 5,637,575
[45] Date of Patent: *Jun. 10, 1997

[54] METHODS OF INHIBITING RESTENOSIS

[75] Inventors: Howard C. Herrmann, Yardley; Elliot Barnathan, Havertown; Paul Weisz, Yardley, all of Pa.

[73] Assignee: The Trustees of the University of Pennsylvania, Philadelphia, Pa.

[*] Notice: The portion of the term of this patent subsequent to May 28, 2008, has been disclaimed.

[21] Appl. No.: 81,493

[22] Filed: Jun. 23, 1993

Related U.S. Application Data

[63] Continuation of Ser. No. 790,320, Nov. 12, 1991, abandoned, which is a continuation-in-part of Ser. No. 691,168, Apr. 24, 1991, abandoned, which is a continuation of Ser. No. 397,559, Aug. 23, 1989, abandoned, which is a continuation-in-part of Ser. No. 434,659, Nov. 9, 1989, Pat. No. 5,019,562, which is a continuation of Ser. No. 295,638, Jan. 10, 1989, abandoned, which is a continuation-in-part of Ser. No. 145,407, Jan. 19, 1988, abandoned.

[51] Int. Cl.$^6$ .................... A61K 31/70; C08B 37/02; C08B 37/16
[52] U.S. Cl. ................ 514/58; 514/54; 536/103
[58] Field of Search .............. 514/54, 58; 536/103

[56] References Cited

U.S. PATENT DOCUMENTS

| | | | |
|---|---|---|---|
| 3,420,788 | 1/1969 | Solms | 260/17.4 |
| 4,020,160 | 4/1977 | Bernstein et al. | 514/58 |
| 4,066,829 | 1/1978 | Nair et al. | 536/103 |
| 4,247,535 | 1/1981 | Lewis et al. | 514/58 |
| 4,258,180 | 3/1981 | Lewis et al. | 536/112 |
| 4,383,992 | 5/1983 | Lipari | 424/238 |
| 4,582,900 | 4/1986 | Brandt et al. | 536/103 |
| 4,596,795 | 6/1986 | Pitha | 514/58 |
| 4,727,064 | 2/1988 | Pitha | 514/58 |
| 4,764,604 | 8/1988 | Müller | 536/103 |
| 4,834,985 | 5/1989 | Elger et al. | 424/488 |
| 4,840,941 | 6/1989 | Ueno et al. | 514/59 |
| 4,877,774 | 10/1989 | Pitha et al. | 514/26 |
| 4,877,778 | 10/1989 | Carpenter et al. | 514/58 |
| 4,902,788 | 2/1990 | Zemel et al. | 536/1.1 |
| 4,929,602 | 5/1990 | Harker et al. | 514/18 |
| 5,019,562 | 5/1991 | Folkman et al. | 514/58 |

FOREIGN PATENT DOCUMENTS

| | | |
|---|---|---|
| 0121777 | 10/1984 | European Pat. Off. |
| 0188821 | 7/1986 | European Pat. Off. |
| 0193850 | 9/1986 | European Pat. Off. |
| 0325199 | 7/1989 | European Pat. Off. |
| 0447171 | 9/1991 | European Pat. Off. |
| 50-36422 | 4/1975 | Japan . |
| 50-140476 | 11/1975 | Japan . |
| 62-123196 | 6/1987 | Japan . |
| 63-122701 | 5/1988 | Japan . |
| 1315401 | 12/1989 | Japan . |
| Wo85/02767 | 7/1985 | WIPO . |
| WO89/06536 | 7/1989 | WIPO . |

OTHER PUBLICATIONS

*The Merck Manual* 15$^{th}$ Ed. (1987) pp. 386–389.
Folkman et al; Science 24:1490–3 (Mar. 1989).
Yamamoto et al; Int. J. Pharm. 49:163–171 (1989).
Powell et al., Low Molecular Weight Heparin Reduces Restenosis After Experimental Angioplasty, *Circulation*, supp. II. vol. 80, No. 4 (Oct. 1989).
Croft et al., *Tetrahedron*, vol. 39, pp. 1417–1474 (1983).
LeVeen et al., *Investigative Radiology*, 17:470–475 (1982).
Nakashima et al., *Antimicrobial Agent and Chemotherapy*, pp. 1524–1528 (1987).
Uekama et al., *International Journal of Pharmaceutics*, vol. 10, pp. 1–15 (1982).
J. Pitha et al., *Journal of Pharmaceutical Sciences*, vol. 75(2), pp. 165–167 (1986).
Yamamoto et al., *International Journal of Pharmaceutics*, vol. 49, pp. 163–171 (1989).
*Chemical Abstracts*, 96:218351u (1982).
Fenyvesi et al., *Chem. Pharm. Bull.*, vol. 32(2), pp. 665–669 (1984).
Fenyvesi et al., *Chem. Pharm. Bull.*, vol. 32(2), pp. 670–677 (1984).
Komiyama et al., *Polymer Journal*, vol. 18(4), pp. 375–377 (1986).
Herrmann, H.C., Abstracts of Papers, National Meeting of the American Heart Association, Anaheim, CA; Nov. 11–14, 1991.
*Chemical Abstracts* 83:79544a (1975).

*Primary Examiner*—Ronald W. Griffin
*Attorney, Agent, or Firm*—Duane, Morris & Heckscher

[57] ABSTRACT

Disclosed are compositions and methods effective for inhibiting restenosis. In particular, the present invention provides compositions for inhibiting undesired smooth muscle cell growth or proliferation following angioplasty in mammals, said composition comprising active agents comprising a very water-soluble derivative of cyclodextrin. The invention also provides methods of inhibiting undesired smooth muscle cell growth or proliferation following angioplasty in mammals comprising orally administering to the mammal a growth-inhibiting amount of an active agent comprising a very water-soluble derivative of cyclodextrin.

12 Claims, 2 Drawing Sheets

METHODS OF INHIBITING RESTENOSIS

This application is a continuation of application Ser. No. 07/790,320 filed Nov. 12, 1991 now abandoned, which is a continuation-in-part of application Ser. No. 07/691,168 filed Apr. 24, 1991 now abandoned, which is a continuation of application Ser. No. 07/397,559 filed Aug. 23, 1989 now abandoned, which in turn is a continuation-in-part of application Ser. No. 07/434,659 filed Nov. 9, 1989 now U.S. Pat. No. 5,019,562, which is a continuation of application Ser. No. 07/295,638 filed Jan. 10, 1989 now abandoned, which in turn is a continuation-in-part of application Ser. No. 07/145,407 filed Jan. 19, 1988 now abandoned.

The present invention is concerned broadly with the inhibition of smooth muscle cell proliferation, and more particularly to the inhibition of smooth muscle cell proliferation following injury to vessel walls caused by treatment of atherosclerosis, such by angioplasty.

Atherosclerosis, which is a disorder involving thickening and hardening of the wall portions of the larger arteries of mammals, is a life-threatening affliction that is largely responsible for coronary artery disease, aortic aneurism and arterial disease of the lower extremities. Atherosclerosis also plays a major role in cerebral vascular disease. In fact, atherosclerosis is responsible for more deaths in the United States than any other disease. See National Center of Health Statistics, Vital Statistics Report, Final Mortality Statistics, 1986.

Angioplasty has heretofore been a widely used method for treating atherosclerosis. For example, percutaneous transluminal coronary angioplasty (hereinafter "PTCA") was performed over 200,000 times in the United States alone during 1988. PTCA procedures involve inserting a deflated balloon catheter through the skin and into the vessel or artery containing the stenosis. The catheter is then passed through the lumen of the vessel until it reaches the stenoic region, which is characterized by a build up of fatty streaks, fibrous plaques and complicated lesions on the vessel wall, which result in a narrowing of the vessel and blood flow restriction. In order to overcome the harmful narrowing of the artery caused by the atherosclerotic condition, the balloon is inflated, thus flattening the plaque against the arterial wall and otherwise expanding the arterial lumen.

Although PTCA has produced excellent results and low complication rates, there has, however, been difficulties associated with the use of this technique. In particular, the arterial wall being enlarged frequently experiences damage and injury during expansion of the balloon against the arterial wall. While this damage itself is not believed to be particularly harmful to the health or the life of the patient, the healing response triggered by this damage can cause a reoccurrence of the atherosclerotic condition. In particular, it has been observed that the smooth muscle cells associated with the stenoic region of the artery initiate cell division in response to direct or inflammatory injury of the artery. As the smooth muscle cells proliferate and migrate into the intimal layer of the artery, they cause thickening of the arterial wall. Initially, this thickening is due to the increased number of smooth muscle cells. Subsequently, however, further thickening of the arterial wall and narrowing of the lumen is due to increased smooth muscle cell volume and accumulation of extracellular matrix and connective tissue. This thickening of the cell wall and narrowing of the lumen following treatment of atherosclerosis is referred to herein as restenosis.

It has been observed that up to 40% of patients who undergo PTCA are afflicted by restenosis and the recurrent arterial blockage that it causes. Thus, the long-term effectiveness of treatments for atherosclerosis, such as by angioplasty, have been substantially limited by the reoccurrence of restenosis.

Techniques have heretofore been developed to prevent restenosis or mitigate its negative consequences. In particular, a variety of pharmacological agents have been evaluated as possible inhibitors of restenosis. One group of pharmacological agents under study are antiplatelet agents. Since platelet aggregation and thrombus formation has been implicated in the development of restenosis, agents that effectively reduce platelet adhesion may be useful in preventing restenosis. An example of this approach is found in U.S. Pat. No. 4,929,602, which discloses halogenmethylketone-containing peptides for use in the prevention of platelet dependent arterial thrombosis.

Another approach to preventing restenosis has been to use pharmacological agents which inhibit smooth muscle cell proliferation. For example, it has been reported that low molecular weight heparin reduces restenosis after transluminal angioplasty. See, Powell et al., *Low Molecular Weight Heparin Reduces Restenosis After Experimental Angioplasty*,—Circulation (Supplement II), Vol. 80, No. 4, October 1989.

Heparin, a mucopolysaccharide, is a constituent of various tissues, especially liver and lung, and mast cells in several mammalian species. However, the use of heparin to inhibit restenosis has several disadvantages. For example, heparin is not a homogeneous, well defined substance, and as a result, the use of such material involves an undesirable lack of predictability and repeatability. That is, heparins manufactured by different processes and different companies may possess differing properties and characteristics. Furthermore, certain forms of heparin are known to possess an anti-coagulant activity which may restrict its use to low dosage levels or to oral administration in order to avoid bleeding.

As best understood, heparin is polydisperse with a molecular weight range from about 5,000 to 40,000. Within a given chain, there are also structural variations such as the varying degrees of sulfation, N-acetylation and C-5 epimerization in the uronic acid residue. Chemically, it has been described as an $\alpha$, $\beta$ glucosidically linked sulfated copolymer of D-glucosamine and D-glucuronic acid.

SUMMARY OF THE INVENTION

Applicants have discovered compositions and methods which are effective for inhibiting restenosis but which do not posses the disadvantages associated with the use of heparin. In particular, the present invention provides compositions for inhibiting undesired smooth muscle cell growth or proliferation following angioplasty in mammals, said composition comprising active agents comprising a very water-soluble derivative of cyclodextrin.

The invention also provides methods of inhibiting undesired smooth muscle cell growth or proliferation following angioplasty in mammals comprising orally administering to the mammal a growth-inhibiting amount of an active agent comprising a very water-soluble derivative of cyclodextrin.

According to certain embodiments of the present invention, the active agent is preferably a very water-soluble derivative of $\alpha$-, $\beta$- or $\gamma$-cyclodextrin, more preferably a very water-soluble cyclodextrin sulfate salt consisting essentially of the sulfated anion of $\alpha$-, $\beta$- or $\gamma$-cyclodextrin associated with a non-toxic physiologically acceptable cation, and even more preferably $\beta$-cyclodextrin tetradecasulfate salt consisting essentially of the sulfated anion of $\beta$-cyclodextrin associated with a non-toxic physiologically acceptable cation.

Thus, applicants have discovered that the oral administration of certain cyclodextrin derivatives are capable of substantially reducing restenosis in mammals. More specifically, applicants have discovered methods and compositions for inhibiting, in vivo, internal proliferation of smooth muscle cells in an artery which has been treated for atherosclerosis, the methods comprising oral administration of very water-soluble cyclodextrin derivatives.

It is thus an object of the present invention to provide methods effective for inhibiting restenosis in mammals.

It is another object of the present invention to provide compositions for inhibiting restenosis in mammals.

These and other objects, aspects and advantages of the present invention will become apparent to those skilled in the art upon reviewing the following description and appended claims.

DETAILED DESCRIPTION OF THE INVENTION

Figure 1A:
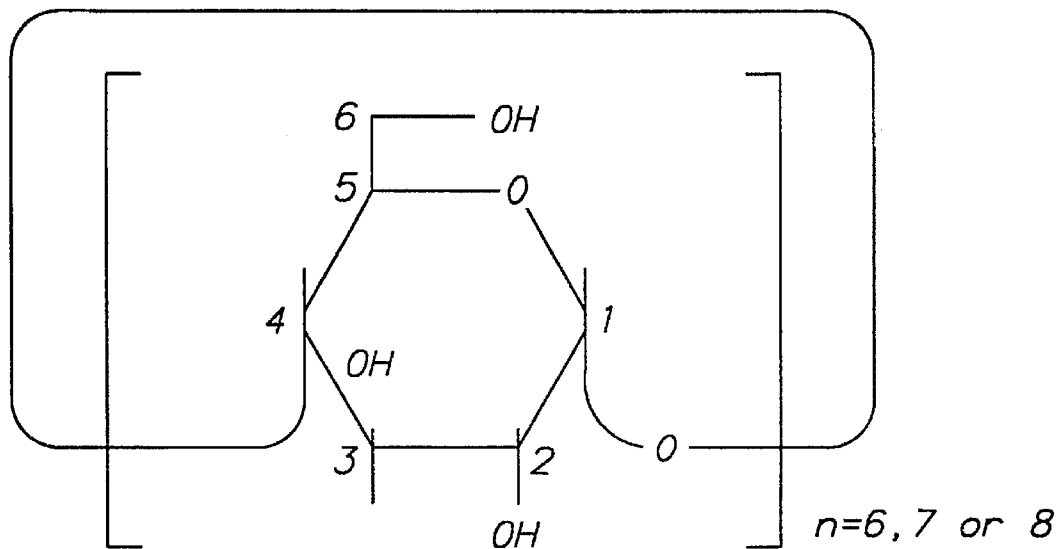
FIG. 1(A and B) is a schematic representation of (A) the chemical structure of α-, β- and γ-cyclodextrins; and (B) of the three-dimensional shape of these cyclodextrins.

Cyclodextrins (hereinafter referred to for convenience as CD or CDs for the singular and the plural, respectively) are cyclic oligosaccharides consisting of at least six glucopyranose units. Although CDs with up to twelve glucopyranose units are known, only the first three homologs have been studied extensively. These compounds have the simple, well-defined chemical structure shown in FIG. 1(A). The common designations of the lower molecular weight α-, β- and γ-CDs are used throughout this specification and will refer to the chemical structure shown in FIG. 1(A) wherein n=6, 7, or 8 glucopyranose units, respectively. The initial discovery of the CDs as degradation products of starch was made at about the turn of the century, and Schardinger showed that these compounds could be prepared by the action of *Bacillus macerans* amylase upon starch. In older literature, the compounds are often referred to as Schardinger dextrins. They are also sometimes called cycloamyloses.

Figure 1B:
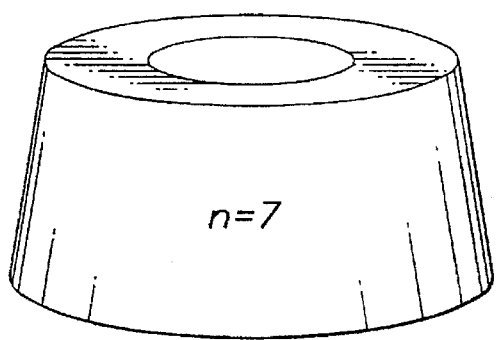

Topographically, the CDs may be represented as a torus, as shown in FIG. 1(B), the upper rim of which is lined with primary —$CH_2OH$ groups, and the lower rim with secondary hydroxyl groups. Coaxially aligned with the torus is a channel-like cavity of about 5, 6 or 7.5 A.U. diameter for the α-, β-, and γ-CDs, respectively. These cavities make the cyclodextrins capable of forming inclusion compounds with hydrophobic guest molecules of suitable diameters.

A reasonably large number of CD derivatives have been prepared and described in the literature. In general, these chemically modified CDs are formed by reaction of the primary or secondary hydroxyl groups attached to carbons 2,3 or 6 [FIG. 1(A)], without disturbing the α (1→4) hemiacetal linkages. A review of such preparations is given in "Tetrahedron Report Number 147, Synthesis of Chemically Modified Cyclodextrins," A. P. Croft and R. A. Bartsch, Tetrahedron 39(9):1417–1474 (1983), incorporated herein by reference in the background (hereinafter referred to as "Tetrahedron Report No. 147"). In particular, α-, β-, and γ-CD sulfates (Na salt) are shown as Compound Nos. 207, 208 and 209 in Tetrahedron Report No. 147 (supra) Table 26, p. 1456.

Applicants have discovered that the oral administration of highly water-soluble cyclodextrin derivatives is effective for inhibiting restenosis in mammals. In particular, β-CD tetradecasulfate (β-CD-TDS) was found to be very effective. In other words, applicants have found that a composition comprising a water-soluble cyclodextrin derivative, such as β-CD tetradecasulfate (β-CD-TDS) is effective, when administered orally according to the teachings herein, for inhibiting or preventing the undesired smooth muscle cell development often observed following angioplasty or treatment to remove atherosclerotic plaques which occlude blood vessels.

Highly water-soluble CD derivatives bearing non-ionic and/or ionic substituents are believed to be useful for inhibiting undesired growth according to the present invention. Suitable highly water-soluble CD derivatives include α-, β- and γ-CD derivatives having non-ionic substituents including but not limited to alkyl substituents such as methyl, ethyl, etc., as well as those in which a number of hydroxyl groups are replaced by other groups so as to increase the hydrophilic activity of the CD. Such groups may include, esters, ethers, thioesters, thioethers, carboxylic acids or other groups which convey hydrophilic activity by way of polar or hydrophilic activity by way of polar or hydrogen bonding constituents or they may include partial hydroxyl substitution that allows better hydrogen bonding involving the remaining hydroxyl groups. Without being bound by or limited to any particular theory, we believe that the hydrophilic activity of the cyclodextrin derivatives of the present invention is roughly indicated by the affinity to water, as measured by water solubility. It is important to measure water solubility at 0° C. since at higher temperatures the most suitable derivatives have solubilities so high that meaningful measurements are difficult. In general, the cyclodextrin derivatives of the present invention have a solubility, measured at 0° C., of at least about 15 gm/100 ml in distilled water, preferably about 30 gm/100 ml. All solubility measurements referred to herein relate to the solubility of the substantially anhydrous derivatives, and when these are salts, to the anhydrous sodium form. The term "very soluble" as used herein refers to a solubility of at least 15 gm/100 ml measured as described above.

It is contemplated that very water-soluble CD derivatives bearing ionic and/or non-ionic substituents may in some instances have advantageous properties, and that these are within the scope of this invention. Although highly water-soluble derivatives in general are believed useful, salt derivatives are preferred.

The phrase "salt derivative" as used herein means an ionic compound derived from a CD by reaction with a suitable reagent. The preferred salt derivatives are provided by a cyclodextrin having substituents selected from the group consisting of sulfate, phosphate, carboxylate and mixtures thereof associated with a non-toxic, physiologically acceptable cation. Many of said preferred derivatives are known compounds. (See, Tetrahedron Report Number 147, supra). But many potentially useful forms may be variants, structurally or chemically of known compounds. They may also possess several different substituents which we believe have not previously been reported. Some of the preferred salt forms of the derivatives are the sodium and potassium forms, since these tend to impart increased water-solubility to organic anions. The salt derivatives useful herein will exhibit electrolytic conductivity and osmotic properties characteristic of electrolytes and polyelectrolytes when in aqueous solution. A particularly preferred salt derivative is β-cyclodextrin tetradecasulfate (β-CD-TDS).

The α-, β- and γ-CD sulfate salts are all believed to be useable in the presently claimed invention. β-CD sulfate salts are preferred. Various degrees of sulfation per glucose unit can be employed, such as an average of one sulfate group per two glucose units or two sulfate groups per glucose unit are preferred. Especially preferred is β-CD-TDS which has an average of two sulfate groups per glucose unit.

According to the present methods, mammals, including humans, which have arterial regions subject to angioplasty are treated by orally administering to the mammal a cyclodextrin derivative of the present invention in an amount effective to inhibit arterial smooth muscle cell proliferation. It is contemplated that the degree of restenosis inhibition according to the present methods may vary within the scope hereof, depending upon such factors as the mammal being treated and the extent of arterial injury during the angioplasty. It is generally preferred, however, that the cyclodextrin derivative be orally administered in an amount effective to cause a substantial reduction in restenosis. As the term is used herein, "substantial reduction in restenosis" means a post treatment restenosis value of no greater than about 50%. According to preferred embodiments, the post treatment restenosis value is no greater than about 25%. As the term is used herein, post treatment restenosis value refers to the restenosis value measured at about one month after angioplasty. The term restenosis value refers to the restenosis rate calculated as a loss of $\geq 50\%$ of the initial gain in minimum lumen diameter achieved by angioplasty.

Thus the present invention contemplates a method of inhibiting restenosis in a patient which comprises orally administering to the patient an amount of a cyclodextrin derivative effective to inhibit the formation of a restenotic lesion in a patient who has undergone angioplasty.

It is contemplated that the cyclodextrin derivative may be administered before, during and/or after angioplasty treatment of the stenosed artery. The compositions and methods of the present invention are typically administered in the form of a liquid solution or suspension comprising cyclodextrin derivative and a suitable, non-toxic physiologically acceptable carrier for the cyclodextrin derivative. As the term is used herein, carrier refers broadly to materials which facilitate administration or use of the cyclodextrin derivative. The liquid solutions or suspensions of the present invention used for oral administration preferably comprise a carrier comprising water and greater than about 40 μg of cyclodextrin derivative per ml of carrier.

It may be desirable to administer a suitable antibiotic as prophylaxis during treatment in accordance with the present invention. Such antibiotics can be mixed with the water-soluble cyclodextrin derivative and administered as a mixture or, alternatively, antibiotics can be administered alone contemporaneously with the water-soluble cyclodextrins either by the same or a different route of administration.

EXAMPLES

The following examples are provided to illustrate this invention. However, they are not to be construed as limiting the scope of the invention, which scope is determined by this entire specification including the appended claims. All amounts and proportions shown are by weight unless explicitly stated to be otherwise.

Examples 1 (A–D)

This example illustrates methods for preparing and purifying cyclodextrin sulfates. The method is not per se considered part of the present invention.

(A) β-CD-TDS(Na)

β-cyclodextrin (99% pure dihydrate) was purchased from Chemalog (a division of General Dynamics Corp.), South Plainfield, N.J.

5.0 grams of β-cyclodextrin (4.4 mmoles, i.e., about 92 meq —OH) was dissolved in 250 ml of dimethyl-formamide (DMF). To this solution was added 15.0 grams of $(CH_3)_3N$—$SO_3$ (108 mmoles) in a single portion and the reaction mixture was heated to 70° C. After two hours at 70° C., a gummy material began to precipitate. The reaction mixture was maintained at 70° C. with vigorous stirring, and then cooled to room temperature. The DMF layer was then decanted and discarded, and the solid residue was dissolved in 250 ml of water followed by addition of 75 ml of 30% sodium acetate. The mixture was stirred vigorously for 4 hours and then poured into 4000 ml of ethanol. After standing overnight, the mixture was filtered to recover the crystallized solids. The filter cake was washed with ethanol (absolute) followed by diethyl ether. The product was then dried under vacuum over $P_2O_5$. 10.3 grams of white powder was recovered. The product was hygroscopic.

The product was analyzed under conditions such that sorption of water was minimized. Elemental analysis gave the following results: C=18.84, H=2.65, S=17.33 (Calculated for $C_6H_8O_{11}S_2Na_2$; C=19.67, H=2.19, S=17.49). $[\alpha]^{22}$=75° (C=2.63 in 0.5M NaCl). The analysis corresponds to that expected for an average substitution of two hydroxyl groups for each glucopyranose unit, i.e., 14 hydroxyls per CD molecules. The calculated yield for such β-CD-TDS salt is 10.96 grams, about 6% higher than the observed 10.3 grams.

(B) α- and γ-CD-$SO_4$ (Na salt)

The procedure described above was used for these preparations except that 86 mmoles of $CH_3N$—$SO_3$ was used with β-CD, and 117 mmoles with the γ-CD.

The sulfated α-CD salt analyzed C=18.76; H=2.60; S=16.22. This corresponds on average to a substitution of about 11.7 hydroxyl units per β-CD molecule.

The sulfated γ-CD salt analyzed C=18.92; H=2.69; S=14.84. This corresponds on average to a substitution of about 14 hydroxyl groups per γ-CD molecule.

(C) β CD-$SO_4$ (Na salt) (7.1 wt %) S)

1.0 gm of β-cyclodextrin was dissolved into 50 ml of DMF. To this solution was added 883 mg of $(CH_3N\ SO_3(7.2$ equivalents). The solution was held at 75° C. for 12 hours, at which time no precipitate had formed. The reaction mixture was cooled to room temperature. To the solution was added 200 ml of ethanol. The resulting colloidal solution was then poured into 600 ml of diethyl ether. A white solid formed in 2 hours. The solid was collected by filtration and then was dissolved in 30 ml $H_2O$. This solution was stirred for 2 hours. After stirring, the solution was poured into 900 ml of 2:1 EtOH-$Et_2O$ solution. Crystals formed over an 8 hour period. The crystals were collected and washed with $Et_2O$. The product was dried over $P_2O_5$ under vacuum. 1.18 gm of powder was recovered. (72.4% yield).

Elemental analysis of the product showed C=32.49; H=4.99; and S=7.06. This corresponds on average to a substitution of about 3.5 hydroxyls per β-CD molecule.

(D) β-CD-Propoxylate~14 $SO_4$

β-CD-(hydroxy-n-propyl ether) was obtained from American Maize-Products Co. (Hammond, Ind.) and the procedure described above was used to prepare the sulfate salt, β-CD-(~4Pr~14 $SO_4$).

Example 2

This example demonstrates that β-CD-TDS is about three times as effective as whole heparin in suppressing smooth muscle cell (SMC) growth when each is used alone (i.e., without exogenous corticosteroid or other supplementation). A bioassay of this activity was made using tissue cultures of rat aortic SMC and calf aortic SMC, with dosages ranging from 0.03 µg/ml up to 400 µg/ml.

Figure 2A:
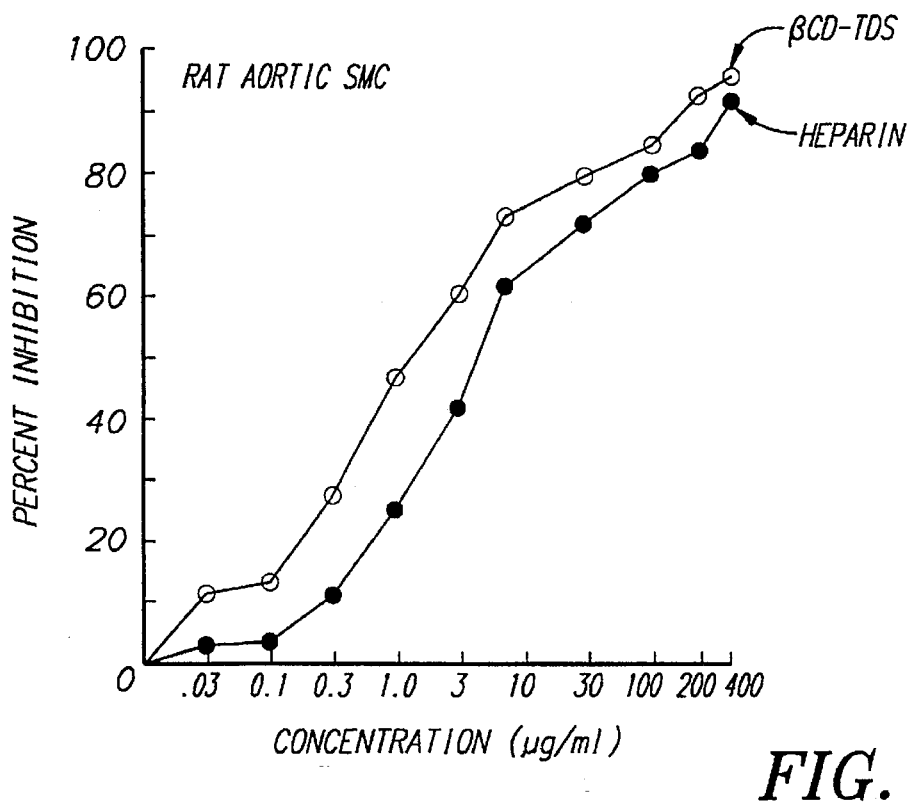
FIG. 2(A and B) graphically illustrates the effect of β-cyclodextrin tetradecasulfate (β-CD-TDS) or heparin on growth of (A) rat aortic smooth muscle cells and (B) calf aortic smooth muscle cells in tissue culture.
Figure 2B:
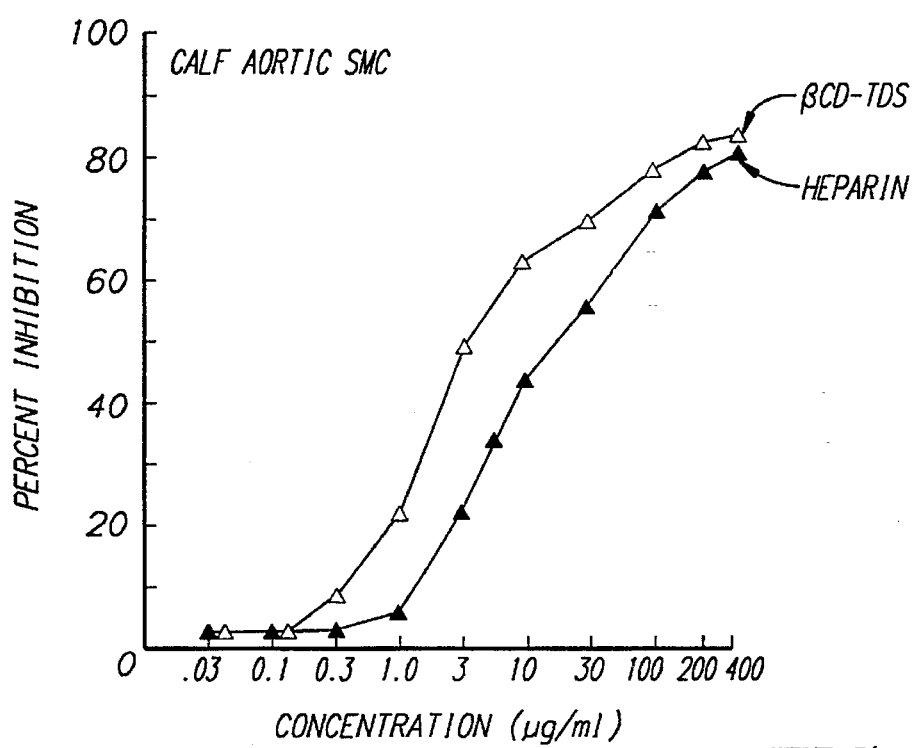

The results are shown graphically in FIG. 2(A) and (B).

Example 3

This example illustrates the inhibition of angioplasty restenosis in New Zealand white rabbits by oral administration of β-CD-TDS. The procedure used according to this Example was substantially similar to the rabbit model described in LeVeen et al., New Rabbit Atherosclerosis Model for the Investigation of Transluminal Angioplasty, Investigative Radiology., 17:470–475 (1982), which is incorporated herein by reference.

New Zealand white rabbits with an average weight of 4 kg (Camm Laboratories) were anesthetized by intramuscular injection of ketamine (40 mg/kg) and xylazine (5 mg/kg). Using sterile technique, the proximal femoral arteries were exposed by cutdown, and a 1 cm segment of artery was isolated with air-tight ligatures. A 27-gauge needle was inserted into the distal portion of the isolated arterial segment, advanced through the lumen and then passed out of the lumen just distal to the proximal ligature. The proximal needle hole served as a vent for perfusate after the needle was then retracted into the lumen. The arterial segment was cleared of blood with a saline perfusion and then perfused with compressed air at a rate of 80 ml/min for 8 minutes. Following air-drying, the isolated segment was cleared of air with a saline flush, and the ligatures were released. Bleeding from the needle puncture sites was controlled by non-occlusive compression for 1 or 2 minutes. The cutdown was closed in known fashion.

Upon recovery from anesthesia the rabbits were placed on an atherogenic diet of 2% cholesterol, 6% peanut oil (Dyets, Inc. Bethlehem, Pa.). The injury produced by air drying the arterial segment resulted in focal fibrocellular lesions of reproducible severity and morphology.

At the end of one month, the animals were anesthetized as described above and peripheral angioplasty was performed with a 2.5 mm diameter polyethylene coronary angioplasty balloon (Mansfield, Inc. Watertown, Mass.). The angioplasty balloon was introduced via cutdown of the carotid artery and was passed across the lesion over a guidewire under fluoroscopic guidance. Animals were anticoagulated by administering 1,000U intra-arterial standard heparin. Two 1-minute inflations of the angioplasty balloon at nominal pressure were performed. Angiograms (diatrizoate meglumine and sodium injection, Squibb) from the distal aorta were performed by hand injection (5 ml) before and 10 minutes after angioplasty. The arterial lesion undergoing angioplasty was assigned on a random basis. In animals with only one lesion (due to contralateral thrombosis), this lesion received angioplasty. Animals with two occluded arteries after air-drying were excluded from the study, and a maximum of one artery per animal received angioplasty and was analyzed.

After angioplasty, animals were randomly divided in two groups of eight, one control group and one treatment group. The control group received normal rabbit chow and normal tap water. The treatment group received normal rabbit chow and drinking water containing 2 mg/ml of β-CD-TDS. In order to estimate the actual drug dosage ingested, the average daily water intake of 8 animals receiving β-CD-TDS was recorded for 12 days and averaged 230±28 ml/day (range 130–327 ml). Using the average weight of the animals, which was about 4 kg, the estimated dosage of β-CD-TDS ranged from about 65 to about 163.5 mg/kg/day., with an average dosage of about 115 mg/kg/day. All animals were treated for one month and β-CD-TDS treatment was started 24 hours before angioplasty.

At the end of this month of treatment, a final angiogram was performed. Euthanasia was performed by administration of 2.5 cc of T-61 solution intravenously. The arteries were then perfusion fixed with 4% buffered glutaraldehyde at 100 mm Hg pressure through the distal descending aorta. The femoral arteries were removed, placed in glutaraldehyde, embedded in paraffin, and cut in 5 micron sections. The sections were then stained with hematoxylin and eosin for microscopic examination.

Intimal hyperplasia was a quantitatively measured via histology. This analysis was performed by digitizing a videomicroscopic image of the stained arterial section on a Macintosh IIx computer using a frame grabber (Quick Capture, Date Translation, Marlboro, Mass.) and Image analysis software (Version 1.27). The areas boarded by the lumen, internal elastic membrane (IEM), and external border of the artery were measured after each of these was traced on the screen. The screen was calibrated in mm using an etched microscope gradicle and the percentage of the arterial cross-sectional area involved by intimal hyperplasia at the narrowest section was calculated as follows:

$$\% \text{ intima} = \frac{\text{area boarded by IEM} - \text{lumen area}}{\text{total arterial area} - \text{lumen area}} \times 100$$

In control femoral arteries undergoing angioplasty, it was observed that the percent of arterial cross-sectional area due to intimal hyperplasia (% intima) was found to be about 50 with a error of about ±1.7%. Animals treated with β-CD-TDS were found to have a degree of intimal hyperplasia of about 27 with an error of about ±2.2%.($p<0.001$).

Angiograms of the femoral arteries in control and β-CD-TDS animals were also performed one month after air injury prior to peripheral angioplasty and quantitatively compared to angiograms 10 minutes after angioplasty and at one month after angioplasty and treatment. All of the angiograms were quantitated by a similar analysis of projected calibrated angiograms. The minimal lumen diameter of each lesion was thus measured by angiogram before, 10 minutes after, and one month after angioplasty. The mean minimum diameter in control animals was found to increase from 1.05±0.1 mm to 1.49±0.1 mm immediately after angioplasty ($p<0.05$) and decrease about 22% to 1.16±0.1 mm one month later ($p$=NS vs pre-angioplasty, $p<0.5$ vs post-angioplasty). In animals treated with β-CD-TDS, the minimum diameter increased from 1.13±0.04 to 1.37±0.1 mm with angioplasty ($p<0.05$), and was unchanged after treatment (1.34±0.1 mm, $p<0.05$ vs pre, $p$=NS vs post-angioplasty). The differences between control and treated animals were significant only at the one month follow up time. Restenosis was defined as a loss of ≧50% of the initial gain in minimal lumen diameter achieved with angioplasty.

The restenosis rate calculated as a loss of ≧50% of the initial gain in minimum lumen diameter achieved by angioplasty was about 75% in control animals and about 25% in animals receiving β-CD-TDS ($p<0.05$).

Data were analyzed using Statview statistical software (Brainpower, Inc., Calabasas, Calif.) and presented as a mean±standard error. Comparisons between treatment groups were made by unpaired two-tailed t-test (angiographic data) or Scheffe's multiple comparison test (histological data), and restenosis rates were compared by Chi-square analysis. Results were considered significant if p<0.05.

In addition to the quantitative analysis described above, morphologic comparisons of arterial cross-sections were performed by light microscopy. Marked intimal hyperplasia was observed and was characterized by a proliferation of spindled cells admixed with variable amounts of fibrosis. Other features included focal collections of foam cells, scattered cholesterol clefts, a general thinning of the media below the areas of intimal hyperplasia and focal disruption of the internal elastic membrane.

Table 1 below summarizes the results of the quantitative testing and analysis described.

TABLE 1

(MLD = minimum lumen diameter; Restenosis = loss > 50% gain)

| Treatment | % intima | ΔMLD (post PTA-final) | Restenosis |
|---|---|---|---|
| Control | 50.5 ± 1.7 | −22.1% | 75% |
| β-CD-TDS | 26.9 ± 2.2* | −2.2% | 25* |

*p < 0.05

Thus, this example illustrates that orally administered β-CD-TDS at dosage rates of from about 65 to about 165 mg/kg/day reduces both intimal hyperplasia and angiographic evidence of restenosis in this rabbit model of angioplasty.

Example 4

This example illustrates the general lack of efficacy observed for oral administration of β-CD-TDS when relatively low dosage rates were used in New Zealand white rabbits. In particular, Example 3 was repeated except that β-CD-TDS was added to the drinking water at 40 µg/ml instead of 2 mg/ml as in the previous example. In order to estimate the actual drug dosage ingested, the average daily water intake of 8 animals receiving β-CD-TDS was recorded for 12 days and averaged 230±28 ml/day (range 130–327 ml). Using the average weight of the animals, which was about 4 kg, the estimated dosage of β-CD-TDS ranged from about 1.3 to about 3.3 mg/kg/day, with an average dosage of about 2.3 mg/kg/day.

It was observed that using dosage levels described in this Example, the treatment group exhibited significantly less improvement in restenosis as compared to the dosage levels described in Example 3. In particular, animals treated with β-CD-TDS had a degree of intimal hyperplasia of about 45.9, while the control group had a degree of intimal hyperplasia of about 50.5

What is claimed is:

1. A method for inhibiting restenosis in mammals after angioplasty comprising orally administering to a mammalian host a liquid composition comprising a sulfated cyclodextrin derivative and a non-toxic, pharmacologically acceptable carrier for said cyclodextrin derivative, the cyclodextrin derivative having a solubility in water of at least about 15 gm/100 ml and being present in said carrier in an amount greater than about 40 µg of cyclodextrin per ml of carrier, said solubility being sufficient for treating restenosis in mammals after said angioplasty.

2. The method of claim 1 wherein said administering step comprises administering said composition in a dosage of from about 65 to about 165 mg/kg of host body weight/day.

3. The method of claim 1 wherein said cyclodextrin derivative is β-cyclodextrin tetradecasulfate.

4. The method of claim 1 wherein said non-toxic, pharmacologically acceptable carrier comprises water.

5. The method of claim 1 wherein the solubility of the cyclodextrin derivative is about 30 g/100 ml.

6. The method of claim 1 wherein the solubility is measured at 0° C. in distilled water.

7. A method for inhibiting restenosis in mammals, after angioplasty, comprising orally administering to a mammalian host a composition comprising a sulfated cyclodextrin derivative and a non-toxic, pharmacologically acceptable carrier for said cyclodextrin derivative, wherein said cyclodextrin derivative is present in an amount greater than about 40 µg of cyclodextrin per ml of carrier for the purpose of treating restenosis in mammals following said angioplasty.

8. The method of claim 7 wherein the cyclodextrin derivative has a solubility in water of at least about 15 gm/100 ml.

9. The method of claim 8 wherein the solubility of the cyclodextrin derivative is about 30 g/100 ml.

10. The method of claim 8 wherein the solubility is measured at 0° C. in distilled water.

11. The method of claim 7 wherein said administering step comprises administering said composition in a dosage of from about 65 to about 165 mg/kg of host body weight/day.

12. The method of claim 7 wherein said cyclodextrin derivative is β-cyclodextrin tetradecasulfate.

* * * * *